(12) United States Patent
Kan et al.

(10) Patent No.: US 7,485,320 B2
(45) Date of Patent: Feb. 3, 2009

(54) LIPOSOME FOR INCORPORATING LARGE AMOUNTS OF HYDROPHOBIC SUBSTANCES

(75) Inventors: Pei Kan, Hsinchu (TW); Ae-June Wang, Hsinchu (TW); Won-Ko Chen, Hsinchu (TW); Chih-Wan Tsao, Pingtung (TW)

(73) Assignee: Industrial Technology Research Institute, Hsinchu (TW)

( * ) Notice: Subject to any disclaimer, the term of this patent is extended or adjusted under 35 U.S.C. 154(b) by 649 days.

(21) Appl. No.: 10/624,362

(22) Filed: Jul. 23, 2003

(65) Prior Publication Data

US 2004/0126886 A1    Jul. 1, 2004

Related U.S. Application Data

(63) Continuation-in-part of application No. 09/866,584, filed on May 30, 2001, now abandoned.

(30) Foreign Application Priority Data

Sep. 25, 2000    (TW) ............................. 89119777 A

(51) Int. Cl.
| | |
|---|---|
| A61K 31/07 | (2006.01) |
| A61K 31/135 | (2006.01) |
| A61K 31/165 | (2006.01) |
| A61K 31/21 | (2006.01) |
| A61K 31/215 | (2006.01) |
| A61K 31/235 | (2006.01) |
| A61K 31/24 | (2006.01) |
| A61K 31/335 | (2006.01) |
| A61K 31/40 | (2006.01) |
| A61K 31/44 | (2006.01) |
| A61K 31/66 | (2006.01) |
| A61K 31/685 | (2006.01) |

(52) U.S. Cl. ............... 424/450; 514/77; 514/114; 514/121; 514/129; 514/283; 514/410; 514/422; 514/426; 514/428; 514/449; 514/511; 514/513; 514/529; 514/532; 514/533; 514/534; 514/617; 514/649; 514/656; 514/725

(58) Field of Classification Search ............... 424/450; 514/77, 114, 121, 129, 283, 410, 422, 426, 514/428, 449, 511, 513, 529, 532, 533, 534, 514/617, 649, 656, 725; 546/48, 49, 50, 546/51, 53; 549/510; 558/166, 169
See application file for complete search history.

(56) References Cited

U.S. PATENT DOCUMENTS

| 4,873,089 A | * | 10/1989 | Scotto et al. ............... 424/450 |
|---|---|---|---|
| 5,415,869 A | * | 5/1995 | Straubinger et al. ......... 424/450 |
| 5,424,073 A | * | 6/1995 | Rahman et al. ............. 424/450 |
| 5,733,572 A | * | 3/1998 | Unger et al. ................ 424/450 |
| 5,776,486 A | * | 7/1998 | Castor et al. ............... 424/450 |

OTHER PUBLICATIONS

Sheih, M. et al Journal of Fermantation and Bioengineering, 1997, 83, 87-90.*
Crosasso, P. et al Journal of Controlled Release, 2000, 63, 19-30.*
Kan, Pei, et al., Formulation of Liposomal Taxol and Process Development, Proceedings of the International Symposium on Controlled Release of Bioactive Materials, 27th, pp. 303-304, Industrial Technology Research Institute, 2000, Controlled Release Society, Inc., Hsinchu, Taiwan.

* cited by examiner

*Primary Examiner*—John Pak
*Assistant Examiner*—Nathan W Schlientz
(74) *Attorney, Agent, or Firm*—Rabin & Berdo, P.C.

(57) ABSTRACT

A liposome formulation for stably incorporating high content of hydrophobic substance is disclosed. The liposome includes two phospholipids with different phase transition temperatures such as saturated and unsaturated phosphatidyl cholines, hydrophobic substances, cholesterol, cholesterol derivatives, antioxidant and hydrophilic polymer-modified lipids such as MPEG-DSPE.

44 Claims, 2 Drawing Sheets

LIPOSOME FOR INCORPORATING LARGE AMOUNTS OF HYDROPHOBIC SUBSTANCES

This application is a continuation-in-part of Ser. No. 09/866,584 filed May 30, 2001, now abandoned.

BACKGROUND OF THE INVENTION

1. Field of the Invention

The invention relates to the use of liposomes in the drug delivery system, and more particularly to the stable liposomes capable of incorporating high content of hydrophobic drugs.

2. Description of the Related Art

Liposome technology has been exploited extensively for the purpose of drug delivery for many years. A typical liposome structure is composed of single or multiple layer membranes with hydrophobic domain between the phospholipid bilayers, and the interior aqueous compartment. Hydrophobic or hydrophilic compounds can be entrapped in the hydrophobic domain or encapsulated in the aqueous compartment, respectively. On the other hand, liposomes can be constructed of natural constituents so that the liposome membrane is in principal identical to the lipid portion of natural cell membranes. It is considered that liposomes are quite compatible with the human body when used as drug delivery system. In addition, liposome-based drug formulation also has been reported to be able to achieve the equivalent therapeutic efficacy to free drug, as well as reduce the systemic toxicity in many applications.

The hydrophobic drug, paclitaxel, was sold in the market in 1992, and used in phase II trials for treating breast and ovarian cancer. In 1998, it was used in combination therapy with cisplatin for the treatment of non-small cell lung and ovarian cancer in phase I trials. However, due to its poor solubility in water, paclitaxel is prepared for clinical administration containing Cremophor EL® (polyethoxylated castor oil) and absolute ethanol in a 50/50 (vol/vol) ratio (Diluent 12). In clinical trials, the problems of anaphylactoid reaction, neutropenia, peripheral neuropathy, bradyarrhythmia and anemia were encountered. Meanwhile, the amount of cremophor EL necessary to solubilize the clinically required dose of paclitaxel is much higher than that administered with any other marketed drug. Cremophor vehicle thus is found to be responsible for hypersensitivity response. Premedication with corticosteroid, diphenhydramine or $H_2$ antagonist, and slow infusion of a large volume are needed to avoid the side effect. In contrast, owing to the aforementioned advantages of liposome-based drug delivery system, researches of incorporating paclitaxel in liposomes for clinical paclitaxel administration have become a hot topic and been reported regularly.

Conventional paclitaxel-liposomes were prepared at paclitaxel/lipid molar ratio of approximately 3 mole % regardless of whether the liposomes are made of a mixture of phosphatidyl glycerol (PG) and phosphatidyl choline (PC) (U.S. Pat. No. 5,415,869; Sampedro, F et al., *J Micrencapsul* 11:309-318 (1993); Sharma, A. et al., *Pharm Res* 11:889-896 (1994); Shien, M. F. et al., *J Ferm Bioeng* 83:87-90 (1997)), or of unsaturated (U.S. Pat. No. 6,090,955; Bartoli, M. H. et al., *J Micrencapsul* 7:191-197 (1990); Riondel, J. et al., *In Vivo* 6:23-28 (1992); Sharma, D. et al., *Melanoma Res* 8:240-244 (1998)) or partially unsaturated PC (U.S. Pat. No. 5,683,715). At a drug/lipid ratio of 4 mole %, the paclitaxel-liposome system is stable only for 2 days while needle-like crystal precipitates appear during preparation at a drug/lipid ratio up to 8 mole % (Sathyamangalam, V. et al., *Biochemistry* 33:8941-8947 (1994); Bernsdorff, C. et al., *J Biomed Mater Res* 46:141-149 (1999)). On the other hand, the liposomes are prepared by employing hydrophilic polymer-conjugated phospholipid (methoxy polyethylene glycol-phosphatidyl ethanolamine) in order to enhance its circulation time in blood post iv administration (Crosasso, P. et al., *J Control Release* 63:19-30 (2000)). Liposomes with the prolonged circulation time in bloodstream make it possible increasing the availability of the injected liposomes to reach the target cells before being metabolized. However, this formulation of the polymer-engrafted liposomes with a maximal 3 mole % (paclitaxel/lipid ratio) quickly become unstable in one-week storage at 4° C.

Alternatively, a formulation of paclitaxel-liposomes comprising a special phospholipid, cardiolipid, and phosphatidyl choline (PC) was disclosed in U.S. Pat. No. 5,424,073 and *Int J Oncol* 12:1035-1040 (Cabanes, A. et al., 1998). The molecular structure of cardiolipid is composed of one huge hydrophilic head and four aliphatic chains. The liposomes prepared in accordance with this formulation increase the paclitaxel/lipid molar ratio to 9 mole %, however, it is stable only for 1 month when stored in liquid form at 4° C.

Generally, paclitaxel incorporated within the bilayer membrane of liposomes is thermodynamically prone to self-aggregation, then precipitating from liposomes. Previous researches have reported that the optimal paclitaxel/lipid molar ratio in a typical liposome formulation is ranged from 3 to 4 mole %, and paclitaxel-liposomes are more stable when the drug/lipid ratio is kept at approximately 3 mole %. When the molar ratio is increased, needle-like crystal precipitates appear during the preparation process. Besides, it is known by person skilled in the art that drugs with a low drug/lipid ratio are commonly unsuitable for clinical administration. A high dose of liposomes still may result in certain extent of toxicity due to the injection of excessive amounts of lipids in the body. Furthermore, increasing liposome concentration also raises the cost of production. Therefore, it is important to elevate the hydrophobic drug/lipid ratio in liposome-based drug delivery system by which the above drawbacks may be avoided.

SUMMARY OF THE INVENTION

It is therefore an object of the invention to provide a liposome-based drug delivery system that is able to incorporate large amounts of hydrophobic compounds. Accordingly, the formulated liposomes capable of incorporating high content of hydrophobic compounds can maintain considerably stable for months, as well as reduce the possible side effects in the versatile applications.

The invention achieves the above-identified objects by providing the formulated liposomes for incorporating large amount of hydrophobic compounds. The composition of the liposomes at least comprises a first and second phospholipids, hydrophobic drugs and other additives such as lipids modified by hydrophilic polymer (such as MPEG-DSPE), cholesterol, cholesterol derivatives and antioxidants. According to the invention, the phase transition temperature of the first phospholipids, $T_{g1}$, is in the range from 40 to 70° C., and preferably from 50 to 65° C. The phase transition temperature of the second phospholipids, $T_{g2}$, is in the range from −30 to 20° C., and preferably from −20 to 4° C. Also, the phase transition temperature of the first phospholipids, $T_{g1}$, is higher than that of the second phospholipids, $T_{g2}$ while the drug delivery temperature $T_1$ and storage temperature $T_2$ are chosen at specified ranges subject to the order of $T_{g1} > T_1 > T_2 > T_{g2}$. The first phospholipids having higher phase transition temperature forms the gel state phase, and the second phospholipids having lower phase transition temperature forms the liquid-crystal phase. Each membrane lipid bilayer consists of several regions of gel state phases and liquid-crystal phases, and the hydrophobic drugs can be held within the lipid bilayer. The phase boundary barrier between the regions of gel state phase and liquid-crystal phase is able to reduce lateral movement and aggregation of the hydrophobic drugs, thereby stabilizing the liposomes. Thus, this liposome composition results in coexistence of multiple discontinuous immiscible phases (gel state phase and liquid-crystal phase) occurring on each bilayer membrane of liposomes regardless of unilamellar or mulitlamellar structure when the drug is delivered or stored. The drug delivery temperature $T_1$ is optionally from 30 to 38° C., while the storage temperature $T_2$ is optionally from 4 to 25° C.

The first phospholipids, with higher phase transition temperature ($T_{g1}$) from 40 to 70° C., are preferably hydrogenated naturally-occurring phospholipids and saturated phospholipids with long carbon chain (—$(CH2)_n$—, the value of n is at least 14), such as phosphatidyl choline (PC), phosphatidyl glycerol (PG), phosphatidyl serine (PS), phosphatidyl acid (PA), or phosphatidyl ethanolamine (PE). Examples of hydrogenated phosphatidyl choline (PC) are hydrogenated egg phosphatidyl choline (HEPC) ($T_g$=50~55° C.) and hydrogenated soy phosphatidyl choline (HSPC) ($T_g$=55° C.), while examples of saturated phsopholipids with long carbon chains (—$(CH2)_n$—, the value of n is at least 14) are dipalmitoyl phosphatidyl choline (DPPC) ($T_g$=42° C.), distearyloyl phosphatidyl choline (DSPC) ($T_g$=55° C.), diarachidoyl phosphatidyl choline (Tg=66° C.), dimyristoyl phosphatidyl ethanolamine (DMPE) (Tg=49.5° C.), dipalmitoyl phosphatidyl ethanolamine (DPPE) (Tg=64° C.), distearoyl phosphatidyl ethanolamine (DSPE) (Tg=74° C.), diarachidoyl phosphatidyl ethanolamine (Tg=82° C.), dipalmitoyl phosphatidyl glycerol (DPPG) (Tg=41.5° C.), distearoyl phosphatidyl glycerol (Tg=54.5° C.), dimyristoyl phosphatidyl acid (DMPA) (Tg=50° C.), dipalmitoyl phosphatidyl acid (DPPA) (Tg=66° C.), dipalmitoyl phosphatidyl serine (DPPS) (Tg=54° C.), and distearoyl phosphatidyl serine (DSPS) (Tg=70° C.). The desired phospholipids may also be a combination of two or more phospholipids listed above. The lists of PC above are illustrations of specific phospholipids but are in no way intended to limit the scope thereof.

The second phospholipids, with lower phase transition temperature ($T_{g2}$) from −30 to 10° C., are preferably unsaturated phospholipids or saturated phospholipids with short carbon chains (—$(CH2)_n$—, the value of n is at most 14), such as phosphatidyl choline (PC), phosphatidyl glycerol (PG), phosphatidyl serine (PS), phosphatidyl acid (PA), or phosphatidyl ethanolamine (PE). Examples of synthetic or naturally-occurring unsaturated phospholipids are egg phosphatidyl choline (EPC) ($T_g$=−8° C.) and soy phosphatidyl choline (SPC) ($T_g$=0° C.), oleoyl palmitoyl phosphatidyl choline (Tg=−10° C.), dioleoyl phosphatidyl choline (Tg=−19° C.), dipetroselinoyl phosphatidyl choline (Tg=1° C.), dipalmitelaidoyl phosphatidyl choline (Tg=−4° C.), dipalmitoleoyl phosphatidyl choline (Tg=−36° C.), dipalmitelaidoyl phosphatidyl ethanolamine (Tg=−33.5° C.), dioleoyl phosphatidyl ethanolamine (Tg=−16° C.), dioleoyl phosphatidyl serine (Tg=−10° C.), while examples of synthetic or naturally-occurring saturated phospholipids with short carbon chains is dilauroyl phosphatidyl choline (DLPC) ($T_g$=−2° C.). diundecanoyl phosphatidyl choline (Tg=−15.5° C.), didecanoyl phosphatidyl choline (Tg=−34.7° C.), dinonanoyl phosphatidyl choline (Tg=−55.2° C.), didecanoyl phosphatidyl ethanolamine (Tg=3.6° C.), dinonanoyl phosphatidyl ethanolamine (Tg=−14.5° C.). The desired phospholipids may also be a combination of two or more phospholipids listed above. The list of phospholipids above are illustrations of specific phospholipids but are in no way intended to limit the scope thereof.

Other objects, features, and advantages of the invention will become apparent from the following detailed description of the preferred but non-limiting embodiments. The following description is made with reference to the accompanying drawings.

Table 1 shows incorporation efficiency of liposomes with different paclitaxel/lipid molar ratios, according to a preferred embodiment of the invention.

Table 2 shows incorporation efficiencies of the liposomes composed of only unsaturated or saturated phosphatidyl cholines at different drug/lipid molar ratios according to a preferred embodiment of the invention.

Table 3 shows the shelf stability of liposomes at different drug/lipid molar ratios according to a preferred embodiment of the invention.

Table 4 shows incorporation efficiency and particle size of different liposome compositions, according to a preferred embodiment of the invention.

Table 5 shows survival rate of mice received i.v. injections of either conventional paclitaxel (Cremophore EL/Ethanol=50/50 (v/v)) or paclitaxel-liposomes at doses of 20 and 40 mg/kg, according to a preferred embodiment of the invention.

DETAILED DESCRIPTION OF THE INVENTION

Figure 1:
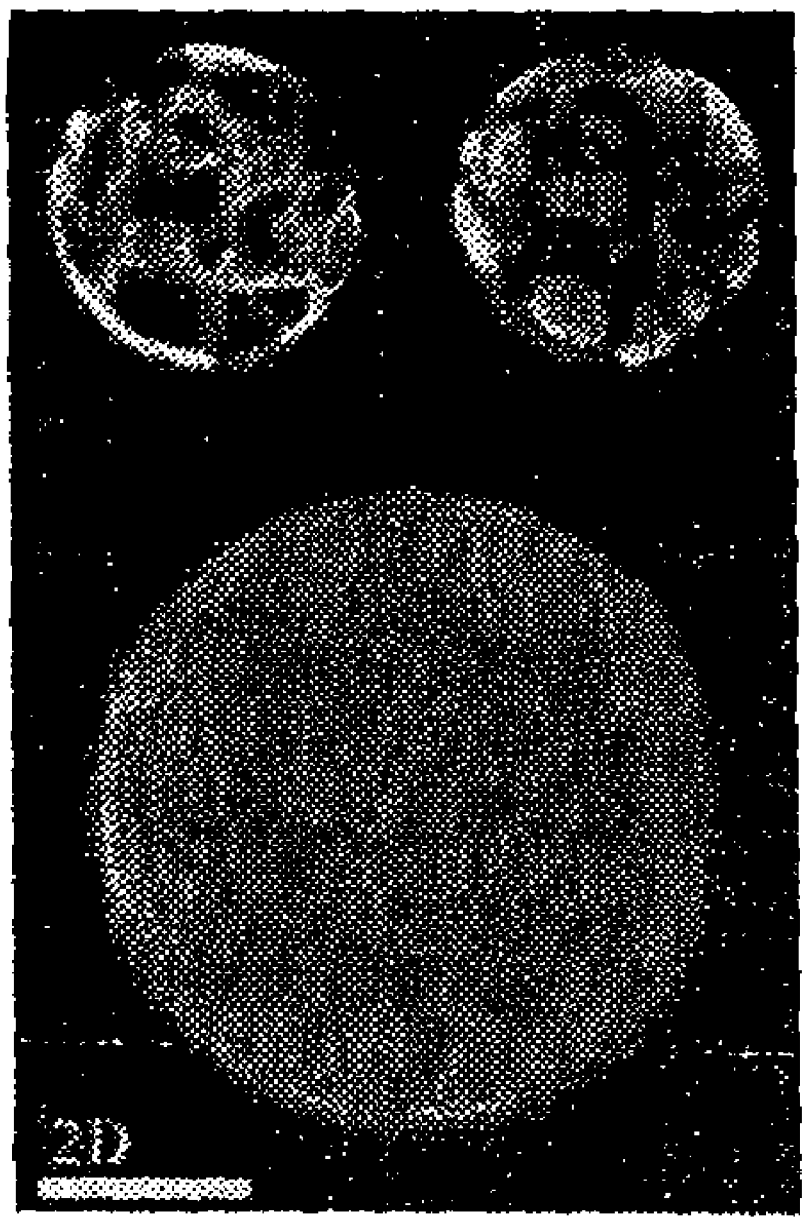
FIG. 1 illustrates that coexisting phenomenon of two phases on the bilayer membrane of liposomes resulting from the liposomes composed of two phospholipids with very different phase transition temperatures.

It is disclosed in the invention that at special ranges of two phospholipid combination and temperature, liposome composed of two phospholipids such as an unsaturated phospholipid (the second phospholipid) and a saturated phospholipid (the first phospholipid ) with different phase transition temperatures are able to form two separated phases, a gel state phase and liquid-crystal phase, in the phospholipid bilayer, as shown in FIG. 1. The two immiscible phases coexist in the liposomes and create several discontinuous regions. The first phospholipid having higher phase transition temperature forms the gel state phase, and the second phospholipid having lower phase transition temperature forms the liquid-crystal phase. Each membrane bilayer consists of several regions of gel state phases and liquid-crystal phases, and the hydrophobic compounds can be held within the lipid bilayer. The phase boundary barrier between the regions of gel state phase and liquid-crystal phase is able to reduce lateral movement and aggregation of the hydrophobic compounds, thereby stabilizing the liposome.

It has been reported that hydrophobic compounds such as paclitaxel has a tendency to undergo concentration-dependent aggregation in hydrophobic environment, forming intermolecular hydrogen bonds (Sathyamanglam, V. et al., *J Pharm Sci* 83: 1470-76(1994)). Similarly, as a large amount of paclitaxel was embedded in the hydrophobic domain within bilayer membrane, it is thermodynamically prone to self-aggregating, destablizing the liposomes. Accordingly, when the formulated liposomes are prepared, two immiscible phases are formed and phase boundaries are speculated to construct a barrier stopping the self-aggregation process of hydrophobic molecules. As a result, stable liposomes capable of incorporating high content of hydrophobic compound become possible. The existence of lateral phase-separated phospholipid-regions is advantageous for incorporating large amount of hydrophobic molecules into the phospholipid bilayer. The formulated liposomes can incorporate higher content of paclitaxel and remain more stable than any other liposome formulations ever reported.

The invention, hence, provides a liposome-based drug delivery system composing of two phospholipids with different phase transition temperatures. The phospholipids with high ($T_{g1}$) and low ($T_{g2}$) phase transition temperatures can be saturated and unsaturated phospholipids, respectively. The coexistence of several discontinuous immiscible phases (e.g. gel phase and liquid-crystal phase) occurs in phospholpiid bilayer at a specific phospholipid composition and temperature (T), wherein $T_{g1}>T>T_{g2}$. The specific temperature T can be the liposome delivery temperature $T_1$ (about 30~38° C.) or storage temperature $T_2$ (about 4~25° C.). Therefore, T is commonly considered as a range that includes the liposome delivery and storage temperatures. The temperature range provides the requirement to design the particular combination of two phospholipids to achieve phase separation. For example, when the intravenous injection is administrated (intravenous administration temperature is 37° C. ($T_1$) and liposomes are stored at is 4° C. ($T_2$)), a phospholipid with phase transition temperature larger than 40° C. ($T_{g1}>40°$ C.) could be carefully chosen as the first phospholipid, and preferably with phase transition temperature ranged from 40 to 70° C. Also, a phospholipid with phase transition temperature lower than 4° C. ($T_{g2}<4°$ C.) could be carefully chosen as the second phospholipid, and preferably in a range from −30 to 4° C. When the subcutaneous injection is administrated (administration temperature is 32° C. ($T_1$) and liposomes are stored at is 25° C. ($T_2$)), a phospholipid with phase transition temperature larger than 35° C. ($T_{g1}>35°$ C.) could be carefully chosen as the first phospholipid, and preferably with phase transition temperature ranged from 35 to 60° C. Also, a phospholipid with phase transition temperature lower than 25° C. ($T_{g2}<25°$ C.) could be carefully chosen as the second phospholipid, and preferably in a range from −20 to 10° C.

The first phospholipids,with higher phase transition temperature ($T_{g1}$) from 40 to 74 0°C, are preferably hydrogenated naturally-occurring phospholipids and saturated phospholipids with long carbon chain (-$(CH2)_n$-, the value of n is at least 14), such as phosphatidyl choline (PC), phosphatidyl glycerol (PG), phosphatidyl serine (PS), phosphatidyl acid (PA), or phosphatidyl ethanolamine (PB). Examples of hydrogenated phosphatidyl choline (PC) are hydrogenated egg phosphatidyl choline (HEPC) ($T_g$=50~55 °C) and hydrogenated soy phosphatidyl choline (HSPC) ($T_g$=55 0C), while examples of saturated phsopholipids with long carbon chains (-$(CH_2)_n$-, the value of n is at least 14) are dipalmitoyl phosphatidyl choline (DPPC) ($T_g$=42 0C), distearyloyl phosphatidyl choline (DSPC) ($T_g$=55 ° C.), diarachidoyl phosphatidyl choline (Tg=66° C.), dimyristoyl phosphatidyl ethanolamine (DMPE) (Tg =49.5 ° C.), dipalmitoyl phosphatidyl ethanolamine (DPPE) (Tg=64° C.), distearoyl phosphatidyl ethanolamine (DSPE) (Tg =74° C.), diarachidoyl phosphatidyl ethanolamine (Tg=82° C.), dipalmitoyl phosphatidyl glycerol (DPPG) (Tg=41.5° C.), distearoyl phosphatidyl glycerol (Tg=54.5° C.), dimyristoyl phosphatidyl acid (DMPA) (Tg=50° C.), dipalmitoyl phosphatidyl acid (DPPA) (Tg=66° C.), dipalmitoyl phosphatidyl serine (DPPS) (Tg=54° C.), and distearoyl phosphatidyl serine (DSPS) (Tg=70° C.). The desired phospholipids may also be a combination of two or more phospholipids listed above.

The second phospholipids, with lower phase transition temperature ($T_{g2}$) from −30 to 10° C., are preferably unsaturated phospholipids or saturated phospholipids with short carbon chains (—$(CH2)_n$—, the value of n is at most 14), such as phosphatidyl choline (PC), phosphatidyl glycerol (PG), phosphatidyl serine (PS), phosphatidyl acid (PA), or phosphatidyl ethanolamine (PE). Examples of synthetic or naturally-occurring unsaturated phospholipids are egg phosphatidyl choline (EPC) ($T_g$=−8° C.) and soy phosphatidyl choline (SPC) ($T_g$=0° C.), oleoyl palmitoyl phosphatidyl choline (Tg=−10° C.), dioleoyl phosphatidyl choline (Tg=−19° C.), dipetroselinoyl phosphatidyl choline (Tg=1° C.), dipalmitelaidoyl phosphatidyl choline (Tg=−4° C.), dipalmitoleoyl phosphatidyl choline (Tg=−36° C.), dipalmitelaidoyl phosphatidyl ethanolamine (Tg=−33.5° C.), dioleoyl phosphatidyl ethanolamine (Tg=−16° C.),dioleoyl phosphatidyl serine (Tg=−10° C.), while examples of synthetic or naturally-occurring saturated phospholipids with short carbon chains is dilauroyl phosphatidyl choline (DLPC) ($T_g$=−2° C.). diundecanoyl phosphatidyl choline (Tg=−15.5° C.), didecanoyl phosphatidyl choline (Tg=−34.7° C.), dinonanoyl phosphatidyl choline (Tg=−55.2° C.), didecanoyl phosphatidyl ethanolamine (Tg=3.6° C.), dinonanoyl phosphatidyl ethanolamine (Tg=−14.5° C.). The desired phospholipids may also be a combination of two or more phospholipids listed above.

The following examples illustrate methods of preparing hydrophobic drugs/liposomes with phospholipids with high or low transition temperatures. The examples are intended to illustrate specific liposome compositions that include the phospholipids listed above, and methods of the invention, but are in no way intended to limit the scope thereof.

EXAMPLE 1

A Method of Preparing Paclitaxel-Liposomes.

In order to prepare a paclitaxel (added amounts)/lipid molar ratio of 1/14, 1.23 mg paclitaxel was added into the alcoholic admixture of the second phospholipid—12.2 mg/ml egg phosphatidyl choline (EPC), the first phospholipid—2.28 mg/ml hydrogenated egg phosphatidyl choline (HEPC), and other additives—2.28 mg/ml cholesterol and 5.4 mg/ml methoxy polyethylene glycol-distearyloyl phosphatidyl ethanolamine (MPEG-DSPE). In the following examples, "MPEG" represents mPEG2000-DSPE, which isregarded to have the same transition temperature as DSPE (i.e.Tg=74° C.).The alcoholic admixture may also contain other antioxidants and cholesterol or cholesterol derivatives. Therefore, the composition of alcoholic admixture illustrated in this example was not to be limited. The solution was evaporated under vacuum to remove the solvent and form a lipid film on the wall of the round-bottom flask at which time, 1 ml, 10% (w/v) sucrose was added to the flask for hydration. Large multilamellar liposomes were suspended, followed by sonicating for 10 mins in order to obtain small unilamellar vesicles. Paclitaxel-containing liposomes were then sterilized by filtration through 0.2 μm cellulose acetate membrane. Laser particle size analyzer (Coulter N4 plus) was used to analyze the particle sizes of the vesicles. The average diameter was approximately 120 nm. After filtration, the concentration of the incorporated paclitaxel in the liposome is determined by HPLC. It was approximately 1.0 mg/ml and the incorporation efficiency was about 80%.

In Example 1, hydrogenated egg phosphatidyl choline (HEPC) selected as the first phospholipid has a phase transition temperature of 50~55° C. which is higher than the intravenous administration temperature (37° C.) and the storage temperature (4° C.). Egg phosphatidyl choline (EPC) selected as the second phospholipid has a phase transition temperature of −8° C. which is lower than the intravenous administration temperature (37° C.) and the storage temperature (4° C.).

EXAMPLE 2

A Method of Preparing Paclitaxel-Liposomes. Procedure is Similar to Example 1 in Addition to Extrusion Unit.

Preparation of the liposomes with the addition of extrusion unit was similar to that in the Example 1. Whereas, the liposomes obtained from sonication or hydration units were followed by extrusion with a series of membranes. Polycarbonate membranes with a uniform pore size ranging from 1.0 to 0.2 μm were used. The pressure from a nitrogen tank provided the driving force. The maximum pressure was set up to 750 psi according to the operation manual of the equipment manufactured by Lipex Co. The resultant liposome sample was sterilized by filtration, too. In this way, a narrow distribution of particle size of liposomes was obtained; the average particle size was estimated to be 150 nm with polydispersity index of 0.3. The loss of the incorporated paclitaxel during the process was about 10%.

EXAMPLE 3

Effect of Increasing Drug/Lipid Ratio

Various aliquots of 10 mg/ml paclitaxel were added into the admixture to change the drug/lipid molar ratio in the liposomes. The method of preparing liposomes was similar to the one described in Example 1. The results are listed in Table 1. Incorporation efficiency of paclitaxel was calculated just after preparation according to the concentration determination by HPLC. It was found (Table 1) that incorporation efficiency was maintained above 80% as the added paclitaxel/lipid molar ratio increases up to 20%. However, incorporation efficiency dropped to 60% when the added paclitaxel/lipid ratio was increased to 25 mole %.

According to these experiments, it is proved that the two immiscible phases (with several discontinuous regions as shown in FIG. 1) coexisting in the liposomes are capable of prevent the self-aggregation of hydrophobic drugs, thereby greatly increasing the amounts of drug held stably within the bilayer of the liposomes. For example, the incorporation amounts (molar %) of paclitaxel had been raised up to 17 mole % when the formula G (Table 1) is conducted. Also, no precipitates appeared during liposome preparation. Moreover, the lipid concentration has no effect on the incorporation amounts (molar %) of paclitaxel (comparison the results of formula B and formula C).

TABLE 1

| Formula | Lipid Conc. (mM) | paclitaxel Added Amount/Lipid (mole %) | Incorporated paclitaxel (mg/ml) | Incorporation Efficiency (%) | Incorporation Amounts (mole %) | Particle Size Average ± SD (nm) |
| --- | --- | --- | --- | --- | --- | --- |
| A* | 40 | 3 | 1.03 | 80.4 | 2.4 | 120.0 ± 45.5 |
| B# | 20 | 7 | 1.04 | 84.5 | 5.9 | 114.3 ± 43.6 |
| C# | 40 | 7 | 2.02 | 82.4 | 5.8 | 115.8 ± 41.0 |

TABLE 1-continued

| Formula | Lipid Conc. (mM) | paclitaxel Added Amount/Lipid (mole %) | Incorporated paclitaxel (mg/ml) | Incorporation Efficiency (%) | Incorporation Amounts (mole %) | Particle Size Average ± SD (nm) |
|---|---|---|---|---|---|---|
| D[#] | 20 | 10 | 1.34 | 78.8 | 7.9 | 116.2 ± 44.1 |
| E[#] | 20 | 13 | 1.60 | 75.0 | 9.8 | 119.0 ± 44.2 |
| F[#] | 20 | 15 | 2.07 | 81.0 | 12.2 | 125.4 ± 46.8 |
| G[#] | 20 | 20 | 2.90 | 85.1 | 17.0 | 134.9 ± 44.6 |
| H[#] | 20 | 25 | 2.32 | 54.6 | 10.9 | 146.3 ± 50.4 |

*Compositions of liposome - second phospholipid EPC:first phospholipid HEPC:other additives (cholesterol/MPEG) = 32:8:(12/2).
[#]Compositions of liposome - second phospholipid EPC:first phospholipid HEPC:other additives (cholesterol/MPEG) = 16:3:(6/2).
Paclitaxel Incorporation Amounts (molar %) = Paclitaxel Added Amounts (molar ratio) × Incorporation Efficiency (%).

COMPARATIVE EXAMPLE 1

Comparison with liposomes made of phospholipids with either high or low transition temperature.

paclitaxel incorporation amounts is 1.0 mol % when two phospholipids, HEPC ($T_g$=50~55° C.) and DPPG ($T_g$=41° C.) both with high transition temperatures, were selected as the first and second phospholipids of liposomes.

TABLE 2

| Liposome Composition (molar ratio) | | | | | Paclitaxel Added | | | | |
|---|---|---|---|---|---|---|---|---|---|
| Second Phospholipid | First Phospholipid HEPC | Other Additives Cholesterol | MPEG | Lipid Conc. (mM) | Amount/ Lipid (mole %) | Incorporated paclitaxel (mg/ml) | Incorporation Efficiency (%) | Incorporation Amounts (mole %) | Particle Size Average ± SD (nm) |
| EPC | | | | | | | | | |
| 20 | — | 8 | 1 | 20 | 3 | 0.45 | 88.4 | 2.7 | 142.9 ± 55.4 |
| 20 | — | 8 | 1 | 20 | 7 | 0.52 | 42.1 | 2.9 | 174.1 ± 71.3 |
| — | 10 | 1 | 1 | 20 | 3 | 0.35 | 68.1 | 2.0 | 3.2 ± 36.1 |
| — | 10 | 1 | 1 | 20 | 3 | 0.35 | 68.1 | 2.0 | 93.2 ± 36.1 |
| DPPG | | | | | | | | | |
| 3 | 7 | 1 | — | 60 | 3 | 1.20 | 34.0 | 1.0 | 118.9 ± 45.2 |

The liposomes composed of only one unsaturated or saturated phosphatidyl cholines (PC) were prepared by the method with similar procedures as described in Example 1. The results were listed in Table 2 and showed that the liposomes made of egg PC was able to incorporate more than 90% paclitaxel only when the added paclitaxel/lipid molar ratio was kept at 3 mole %. However, incorporation efficiency dropped to 40% once the molar ratio was raised up to 7 mole %. If the added paclitaxel/lipid molar ratio was raised up to 7 mole %, the incorporation efficiency dropped to 40%.

Also, the liposomes made of only HEPC could not incorporate more than 3 mole % of paclitaxel. The incorporation efficiency was estimated to be 40-60% when the added paclitaxel/lipid ratio was 3 mole %.

Compare the results (Table 2) with Example 3 (Table 1), it indicated that the liposomes made of the phospholipids only with either high or low transition temperature can not achieve the object of incorporating high content of hydrophobic drugs. The paclitaxel incorporation amount of the liposomes mostly made of EPC is not more than 3 mol % (Table 2). The paclitaxel incorporation amounts of the liposomes mostly made of HEPC is only about 2 mol % (Table 2). Moreover, the

EXAMPLE 4

Stability of Paclitaxel-Liposome Stored at 4° C.

Paclitaxel-liposomes prepared by different molar ratio of liposome compositions (listed in Table 3) were stored at 4° C. immediately after liposome-forming process. Paclitaxel crystals and liposomes with large particle sizes were removed by filtration through 0.2 μm CA-membrane. The concentration of paclitaxel was determined by HPLC. The results were listed in Table 3. According to these experiments of Example 4, it has disclosed that the liposomes comprising EPC and HEPC and added large amount of paclitaxel are greatly stable, and are even stable after 6-month storage. As indicated in Table 4, the incorporation efficiency of the liposomes, originally having the added paclitaxel/lipid ratio of 20 mole %, had dropped to 69% of initial incorporation efficiency after 6-month storage. However, the incorporation efficiency of the liposomes, that originally has the added paclitaxel/lipid ratio of 15 mole %, had been at over 85% of initial incorporation efficiency after 6-month storage. It has been proved that the two immiscible phases (with several discontinuous regions as shown in FIG. 1) coexisting in liposomes not only prevent the self-aggregation of hydrophobic drugs, thereby greatly increasing the amount of drugs held within the bilayer of the liposomes, but also prolong the storage time without deteriorating the stability of the liposomes.

The results of Table 3 also indicated that the incorporation efficiency of the liposomes comprising only one phospholipid (EPC or HEPC only) were low and had dropped quickly after one-month storage, especially the one-lipid liposomes incorporated with a high added paclitaxel/lipid ratio. For example, the incorporation efficiency of the liposomes, using EPC as the only lipid and originally having the added paclitaxel/lipid ratio of 7 mole %, had dropped to 67.8% and 35.4% of initial incorporation efficiency after 14-day and 1-month storage, respectively. This result showed that the liposomes made of one lipid didn't increase the incorporation efficiency and stability of the liposomes; in contrast, the liposomes made of at least two lipids having the said different phase transition temperatures can incorporate high content of hydrophobic drugs and remain stable. Moreover, when a molar ratio of the first phospholipids (HEPC) to the second phospholipid (EPO) is 3/16, the liposomes can incorporate high content of hydrophobic druas (such as 7 mole% to 25 mole% of paclitaxel) and remain in a very stable condition. For example, as shown in the Table 3, when a molar ratio of the first phospholipid to the second phospholipid is 3/16 and 7 mole% of the paclitaxel is incorporated, the incorporation efficiency is 105.3% after 14-day and remains 107% after 6-month storage. When a molar ratio of the first phospholipid to the second phospholipid is 3/16 and 20 mole% of the paclitaxel is incorporated, the incorporation efficiency is 91.7% after one-month storage and still remains 69% after 6-month storage. Also, when 25 mole% of the paclitaxel is incorporated (first/second lipids =3/16), the incorporation efficiency is 99.6% after one-month storage and still remains 73.3% after 2-month storage. Thus, when a molar ratio of the first phospholipid (MPEG) to the second phospholipid (EPO) is egual to or larger than 3/16, the liposomes can incorporate high content of hydrophobic drugs and remain the drug at a stable condition in a significant period.

EXAMPLE 5

Effects of Different Lipid Source and Lipid Composition.

Paclitaxel-liposomes were prepared along with the procedure as described in Example 1. Hydrogenated egg phosphatidyl choline (HEPC) or hydrogenated soy phosphatidyl choline (HSPC) is selected as the first phospholipid. Egg phosphatidyl choline (EPC) is selected as the second phospholipid, the same as Example 1. Also, these experiments of example 5 were conducted to evaluate the influence of lipid ratio on the paclitaxel incorporation efficiency by changing the HEPC/lipid ratio or HSPC/lipid ratio. The results are listed in Table 4.

The results indicated that the liposomes with different particle sizes and incorporated amounts can be obtained by adjusting the HEPC/lipid ratio. Besides HEPC, the phospholipid from different sorts, such as HSPC, can be chosen as the first phospholipid. Soy phosphatidyl choline (SPC) is extracted from the soy beans. Hydrogenated soy phosphatidyl choline (HSPC) generally has a longer chain than hydrogenated egg phosphatidyl choline (HEPC). Consequently, the liposomes with larger particle size can be obtained if using HSPC as the first phospholipid. Also, this result demonstrated that the hydrogenated phosphatidyl choline (HPC) purified from specific species could carry a high content of lipophilic (hydrophobic) drug. However, the optimal HPC/lipid ratio with the maximum incorporation efficiency depended on the combination of the selected phospholipids.

Example 5, egg phosphatidyl choline (EPO) selected as the second phospholipid has a phase transition temperature of -8 °C which is lower than the intravenous administration temperature (37°) and the storage temperature (4°) Hydrogenated soy phosphatidyl choline (HSPC) selected as the firsf phospholipid has a phase transition temperature of 55~60 which is higher than the intravenous administration temperature (37°) and the storage temperature (4°); therefore, HSPC can be combined with the second phospholipid (i.e. EPC) to compose the liposomes.

TABLE 3

| Liposome Composition (molar ratio) | | | | Paclitaxel Added | | | Incorporation Efficiency (%)* | | | | |
| --- | --- | --- | --- | --- | --- | --- | --- | --- | --- | --- | --- |
| Second Phospholipid | First Phospholipid | Other Additives | | Amount/ Lipid | Lipid Conc. | Incorporated Paclitaxel[#] | 14 Days | One Month | Two Months | Three Months | Six Months |
| EPC | HEPC | Cholesterol | MPEG | (mole %) | (mM) | (mg/ml) | | | | | |
| 20 | — | 8 | 1 | 3 | 20 | 0.49 | 89.3 | 77.9 | Dis-integrated | | |
| 20 | — | 8 | 1 | 7 | 20 | 0.45 | 67.8 | 35.4 | Dis-integrated | | |
| — | 10 | 1 | 1 | 3 | 20 | 0.32 | 76.7 | 63.6 | Dis-integrated | | |
| 32 | 8 | 12 | 2 | 3 | 40 | 0.77 | 108.4 | N/A | 73.9 | N/A | N/A |
| 16 | 3 | 6 | 2 | 7 | 20 | 0.92 | 105.3 | 97.9 | 104.6 | 92.2 | 107.0 |
| 16 | 3 | 6 | 2 | 7 | 40 | 2.02 | 104.4 | 97.3 | 105.0 | N/A | N/A |
| 16 | 3 | 6 | 2 | 10 | 20 | 1.34 | N/A | 90.0 | 99.5 | 93.3 | 94.8 |
| 16 | 3 | 6 | 2 | 13 | 20 | 1.60 | N/A | 93.7 | 98.5 | 87.5 | 89.4 |
| 16 | 3 | 6 | 2 | 15 | 20 | 2.07 | 94.2 | 109.7 | 86.0 | 86.1 | 85.1 |
| 16 | 3 | 6 | 2 | 20 | 20 | 2.90 | 88.7 | 91.7 | 85.5 | 82.2 | 69.0 |
| 16 | 3 | 6 | 2 | 25 | 20 | 2.32 | N/A | 99.6 | 73.3 | N/A | N/A |

[#]The initial concentration of incorporated paclitaxel.
*Incorporation Efficiency = concentration of incorporated paclitaxel at the N-the day/the initial concentration of incorporated paclitaxel

TABLE 4

| | Liposome Composition (molar ratio) | | | | | Average | |
|---|---|---|---|---|---|---|---|
| Drug | Second Phospholipid | First Phospholipid | | Other Additives | | Incorporation Efficiency | Particle Size |
| Paclitaxel | EPC | HEPC | HSPC | Cholesterol | MPEG | (%)[#] | (nm) |
| 0.3 | 8 | 2 | | 1 | 0.5 | 69.2 | 113.3 |
| 0.3 | 6 | 4 | | 1 | 0.5 | 63.8 | 120.8 |
| 0.3 | 4 | 6 | | 1 | 0.5 | 73.6 | 128.4 |
| (0.3) | 8 | | 2 | 1 | 0.5 | 82.2 | 149.5 |
| 0.3 | 6 | | 4 | 1 | 0.5 | 62.2 | 167.8 |

[#]Incorporation Efficiency = paclitaxel incorporated in liposome/paclitaxel added amounts.
MPEG—methoxy polyethylene glycol-distearyloyl phosphatidyl ethanolamine.

EXAMPLE 6

Effect of Cholesterol Content of Liposomes.

Varying cholesterol content affected the incorporation efficiency and particle size of liposomes. Also, incorporation of cholesterol could enhance the rigidity of liposomes. It is believed that the circulation time through i.v. administration is prolonged due to the enhanced rigidity of the liposomes.

Figure 2:
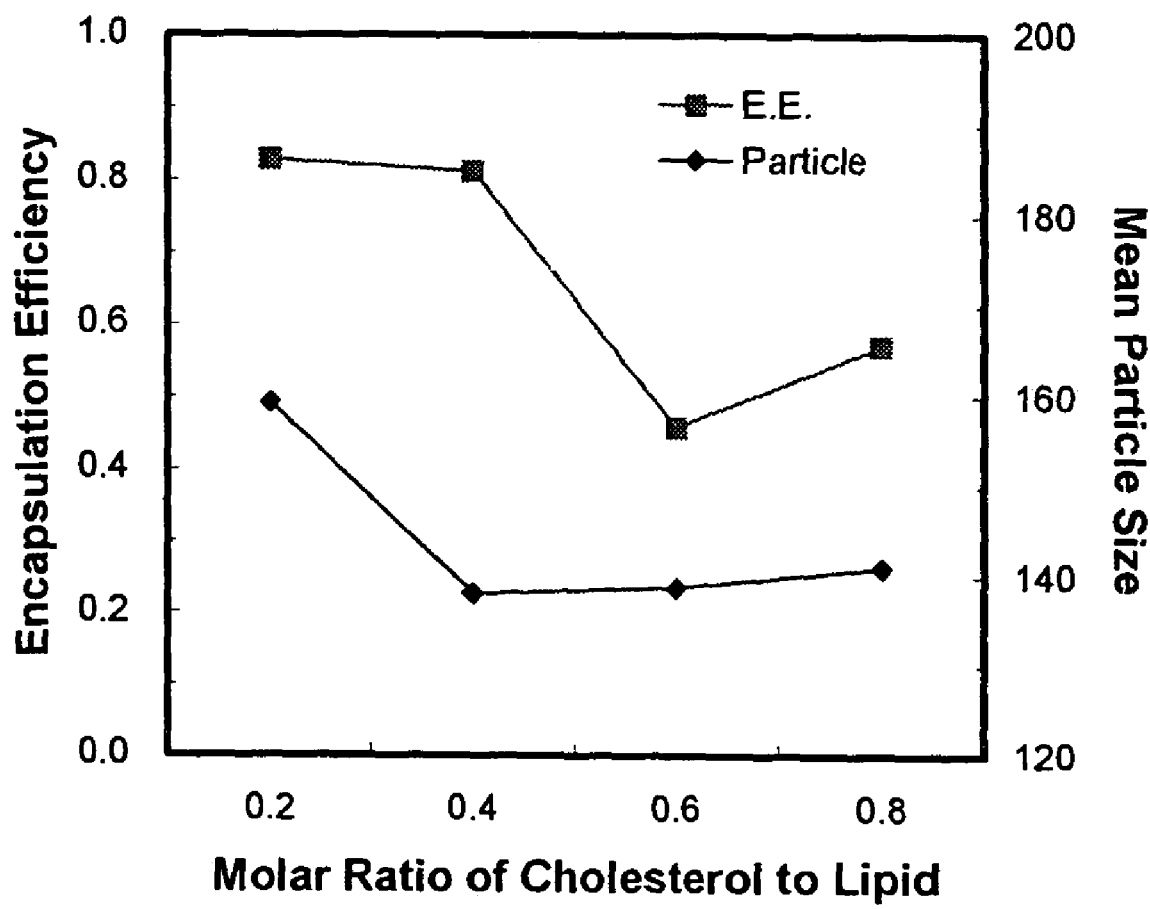
FIG. 2 illustrates that the incorporation efficiency and particle size of liposomes are affected by altering cholesterol content according to a preferred embodiment of the invention.

FIG. 2 illustrates that the incorporation efficiency and the particle sizes of the liposomes are affected by altering the cholesterol content according to a preferred embodiment of the invention. In the general formulation shown in FIG. 2, increasing cholesterol content usually reduced the incorporation efficiency of paclitaxel as well as the average particle size of the liposomes. Since the cholesterol was trapped in the phospholipid bilayer, the amounts of the cholesterol had the effect on the quantities of lipophilic drug that is also held within the phospholipid bilayer. Accordingly, the need for cholesterol addition depends on the different combination of lipids and lipophilic drug. In order to achieve the best incorporation efficiency and the appropriate particle size of the liposomes, an optimal range of cholesterol content has to be determined first. The results in FIG. 2 indicated that the optimal range of cholesterol content for paclitaxel-liposome system is about 0.2~0.3 in term of cholesterol/lipid molar ratio.

EXAMPLE 7

Storage Method of the Paclitaxel-Liposomes.

Paclitaxel-liposomes were stored at −20 or −75° C. after the preparation process. Particle size and paclitaxel concentration were measured periodically. The results indicated that paclitaxel-liposomes stored at −75° C. was stable for at least 3 months. Also, the liposomes could be lyophilized, and then stored in lyophilized cake at 4° C. for several months.

EXAMPLE 8

Incorporation of Large Amounts of All-Trans Retinoic Acid (ATRA) in the Liposomes.

The liposome system of the invention can be also used for incorporating other hydrophobic drugs, such as retinoic acid. To prepare a drug added amounts/lipid molar ratio of 1/3, 2 mg all-trans retinoic acid (ATRA) was added into the alcoholic admixture of 12.2 mg/ml egg phosphatidyl choline (EPC), 2.28 mg/ml hydrogenated soy phosphatidyl choline (HSPC), 2.28 mg/ml cholesterol, and 5.4 mg/ml methoxy polyethylene glycol-distearyloyl phosphatidyl ethanolamine (M PEG-DSPE). The alcoholic admixture may also contain other antioxidants or cholesterol derivatives. Therefore, the composition of alcoholic admixture of this example is used for illustrating sense, rather in a restricted sense. The solution containing ATRA was evaporated under vacuum to remove solvent, and a lipid film was formed on the wall of the round-bottom flask. After evaporation, the lipid film was hydrated with 1 ml, 10% (w/v) of sucrose to produce suspensions of multilamellar vesicles. Then, the liposome suspension was sonicated for 10 mins to obtain smaller unilamellar vesicles. Retonic acid-containing liposomes then were sterilized by filtration through 0.2 μm CA-membrane. Particle size was analyzed by laser particle size analyzer, and the average diameter was approximately 160 nm. After filtration, the concentration of retinoic acid incorporated in liposomes was determined by H PLC, and was approximately 1.9 mg/ml. The incorporation efficiency was more than 90%, and ATRA/lipid ratio was up to 33 mole%.

The liposomes, prepared by the procedure described above, can also encapsulate large amounts of ATRA. Accordingly, the liposomes prepared by description of example is able to encapsulate all of retinoic acid and its derivatives. A drug/lipid ratio range for incorporation of retinoic acid and its derivatives is 1 mole%40 mole%, and people who skill in the art are able to use and make the same.

EXAMPLE 10

Incorporation of Large Amounts of Camptothecin in the Liposomes.

To prepare a drug added amounts/lipid molar ratio of 3/10, 2 mg camptothecin was added into the admixture of 12.2 mg/ml egg phosphatidyl choline (EPC), 2.28 mg/ml hydrogenated egg phosphatidyl choline (HEPC), 2.28 mg/ml cholesterol and 5.4 mg/ml methoxy polyethylene glycol-distearyloyl phosphatidyl ethanolamine (MPEG-DSPE). The solution containing camptothecin was evaporated under vacuum to remove solvent, and a lipid film was formed on the wall of the round-bottom flask. After evaporation, the lipid film was hydrated with 1 ml, 10% (w/v) of sucrose to produce suspensions of multilamellar vesicles. Then, the liposome suspension was sonicated for 10 mins to obtain smaller unilamellar vesicles. Particle size was analyzed by laser particle size analyzer, and the average diameter was approximately 148 nm. Also, no visible precipitate (crystallization of camptothecin) appears during preparation. The camptothecin/lipid ratio was up to 30 mole %.

The liposomes, prepared by the procedure described above, can incorporate large amounts of camptothecin. Accordingly, people who skill in the art are able to know that the liposomes system prepared by description of example should be able to incorporate all of camptothecin derivative, and a drug/lipid ratio for incorporation of camptothecin and its derivatives is 1 mole%40 mole Examples 1, 2, 9 and 10 have indicated that the liposomes prepared according to the invention can incorporate large amounts of paclitaxel and its derivative, retinoic acid and its derivative, and camptothecin and its derivative. In accordance with this aspect of the invention, the liposomes, which are not limited to incorporate the compounds listed above, are capable of incorporating large amounts of paclitaxel anc its derivative, retinoic acid and its derivative, camptothecin and its derivative, and mixture of combining two or more compounds listed above.

EXAMPLE 11

Toxicity of Conventional Paclitaxel and Paclitaxel-Liposomes.

Four groups of five to six-week-old male ICR mice received intravenous injections of either conventional paclitaxel delivery system (cremophore EL/ethanol=1/1) or paclitaxel-liposome delivery system at doses of 20 and 40 mg/kg. Survival rate in all the groups was recorded over 14 days, and the results were listed in Table 5. The toxicity surveys indicated that the conventional paclitaxel delivery system caused 20% loss of mice (1/5), which received a dose of 20 mg/kg, within 14 days, and caused a sudden loss of 100% of mice (5/5) which received a dose of 40 mg/kg. However, the group of mice administrated by the dose of 40 mg/kg of the paclitaxel-liposome delivery system of the invention were survived over 14 days. Consequently, the paclitaxel-liposome delivery system of the invention does decrease the toxicity in comparison to conventional paclitaxel formulation.

TABLE 5

|  | Dose (mg/kg) | Survival Rate |
| --- | --- | --- |
| Conventional Paclitaxel delivery system | 20 | 4/5 |
|  | 40 | 0/5 |
| Liposomal Paclitaxel delivery system of the invention | 40 | 8/8 |

According to the aforementioned description, the liposomes of the invention can incorporate the hydrophobic compounds such as paclitaxel in a drug/lipid ratio up to 20 mole %, and the variation of incorporation efficiency and particle size were within 15% when the liposomes were stored at 4° C. over 6 months.

In comparison with the reported formulation of paclitaxel-liposome, the drug/lipid ratio was increased to about 20 mole % by using the present liposome compositions of the invention. The dramatic improvement resulted from the composition of two phospholipids with different physical properties.

It had been discovered that two phospholipids with different phase transition temperatures created immiscible two phases, and these discontinuous regions coexisting in the liposomes could prevent paclitaxel from self-aggregation and precipitation (needle-like crystals). Even the liposomes that contained large amounts of drugs could be maintained stable to a certain extent. In accordance with this theory, the formulation of liposomes of the invention could be applied to incorporate other hydrophobic drugs that easily precipitated during the preparation or storage such as all-trans retinoic acid. According to the experiments of the invention, the liposomes of the invention increased the maximum ATRA/lipid ratio to 33 mole % while conventional formulations of liposomes had the maximum ATRA/lipid ratio of 20 mole %. Additionally, the more the difference between the phase transition temperatures of two phospholipids is, the larger quantities of the hydrophobic drug are incorporated in the liposomes.

While the invention has been described by way of example and in terms of preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A formulated liposome for incorporating a high content of hydrophobic substances therein, comprising:
    a first phospholipid which is selected from the group consisting of a hydrogenated naturally-occurring phospholipid and a saturated phospholipid having long carbon chains (—(CH2)$_n$—, in which n is at least 14), and which has a phase transition temperature $T_{g1}$ ranging between 40 and 74° C.;
    a second phospholipid which is selected from the group consisting of an unsaturated phospholipid and a saturated phospholipid having short carbon chains (—(CH2)$_n$—, in which n is at most 14), and which has a phase transition temperature $T_{g2}$ ranging between −30 and 10° C.;
    liposome-forming materials effective to form a liposome in which the first phospholipid and the second phospholipid coexist in two immiscible phases and create several discontinuous regions, and in which a molar ratio of the first phospholipid to the second phospholipid is at least 3:16; and
    one or more hydrophobic substances incorporated in the liposome in an amount of at least 20 mole % to form the formulated liposome, wherein a drug delivery temperature $T_1$ and a drug storage temperature $T_2$ are chosen at specified ranges subject to an order of $T_{g1}>T_1>T_2>T_{g2}$, and wherein the formulated liposome has an incorporation efficiency which remains at least about 70% of incorporation efficiency for six months or more.

2. The formulated liposome according to claim 1, wherein the phase transition temperature of the first phospholipid ranges between 50 and 65° C., and the phase transition temperature of the second phospholipid ranges between −20 and 4° C.

3. The formulated liposome according to claim 1, wherein the first phospholipid is selected from the group consisting of phosphatidyl choline (PC), phosphatidyl glycerol (PG), phosphatidyl serine (PS), phosphatidyl acid (PA) and phosphatidyl ethanolamine (PE).

4. The formulated liposome according to claim 3, wherein the first phospholipid is selected from the group consisting of hydrogenated egg phosphatidyl choline (HEPC), hydrogenated soy phosphatidyl choline (HSPC), dipalmitoyl phosphatidyl choline (DPPC) and distearyloyl phosphatidyl choline (DSPC), diarachidoyl phosphatidyl choline, dimyristoyl phosphatidyl ethanolamine (DMPE), dipalmitoyl phosphatidyl ethanolamine (DPPE), distearoyl phosphatidyl ethanolamine (DSPE), dipalmitoyl phosphatidyl glycerol (DPPG), distearoyl phosphatidyl glycerol, dimyristoyl phosphatidyl acid (DMPA), dipalmitoyl phosphatidyl acid (DPPA), dipalmitoyl phosphatidyl serine (DPPS), and distearoyl phosphatidyl serine (DSPS).

5. The formulated liposome according to claim 1, wherein the second phospholipid is selected from the group consisting of phosphatidyl choline (PC), phosphatidyl glycerol (PG), phosphatidyl serine (PS), phosphatidyl acid (PA) and phosphatidyl ethanolamine (PE).

6. The formulated liposome according to claim 5, wherein the second phospholipid is selected from the group consisting of egg phosphatidyl choline (EPC), soy phosphatidyl choline (SPC), oleoyl palmitoyl phosphatidyl choline, dioleoyl phosphatidyl choline, dipetroselinoyl phosphatidyl choline, dipalmitelaidoyl phosphatidyl choline, dioleoyl phosphatidyl ethanolamine, dioleoyl phosphatidyl serine, dilauroyl phosphatidyl choline (DLPC), diundecanoyl phosphatidyl choline, didecanoyl phosphatidyl ethanolamine, and dinonanoyl phosphatidyl ethanolamine.

7. The formulated liposome according to claim 1, wherein the hydrophobic substances are one or more hydrophobic pharmaceutical compounds.

8. The formulated liposome according to claim 7, wherein the one or more hydrophobic pharmaceutical compound is paclitaxel.

9. The formulated liposome according to claim 8, wherein the paclitaxel is incorporated with a drug/lipid ratio ranging from at least 20 mole % to 25 mole %.

10. The formulated liposome according to claim 9, wherein the paclitaxel is incorporated with a drug/lipid ratio ranging from at least 20 mole % to 25 mole % when the first phospholipid is hydrogenated egg phosphatidyl choline (HEPC) and the second phospholipid is egg phosphatidyl choline (EPC).

11. The formulated liposome according to claim 9, wherein the paclitaxel is incorporated with a drug/lipid ratio ranging from at least 20 mole % to 25 mole % when the first phospholipid is hydrogenated soy phosphatidyl choline (HSPC) and the second phospholipid is egg phosphatidyl choline (EPC).

12. The formulated liposome according to 7, wherein the hydrophobic pharmaceutical compound is retinoic acid.

13. The formulated liposome according to claim 12, wherein the retinoic acid is incorporated with a drug/lipid ratio ranging from at least 20 mole % to 40 mole %.

14. The formulated liposome according to claim 13, wherein the retinoic acid is incorporated with a drug/lipid ratio ranging from at least 20 mole % to 40 mole % when the first phospholipid is hydrogenated soy phosphatidyl choline (HSPC) and the second phospholipid is egg phosphatidyl choline (EPC).

15. The formulated liposome according to claim 7, wherein the hydrophobic pharmaceutical compound is camptothecin.

16. The formulated liposome according to claim 15, wherein the camptothecin is incorporated with a drug/lipid ratio ranging from at least 20 mole % to 30 mole %.

17. The formulated liposome according to claim 16, wherein the camptothecin is incorporated with a drug/lipid ratio ranging from at least 20 mole % to 30 mole % when the first phospholipid is hydrogenated egg phosphatidyl choline (HEPC) and the second phospholipid is egg phosphatidyl choline (EPC).

18. The formulated liposome according to claim 7, wherein the hydrophobic pharmaceutical compound is selected from the group consisting of paclitaxel retinoic acid, and camptothecin.

19. The formulated liposome according to claim 1, wherein the liposome-forming materials are selected from the group consisting of hydrophilic polymer-modified lipids, cholesterol, antioxidant, and mixtures thereof.

20. The formulated liposome according to claim 19, wherein the hydrophilic polymer-modified lipid is methoxy polyethylene glycol-distearyloyl phosphatidyl ethanolamine (MPEG-DSPE).

21. The formulated liposome according to claim 1, wherein the one or more hydrophobic substances incorporated in the liposome is present in an amount of ranging from at least 20 mole % to about 25 mole %.

22. The formulated liposome according to claim 1, wherein the one or more hydrophobic substances incorporated in the liposome is present in an amount ranging from at least 20 mole % to about 25 mole.

23. The formulated liposome according to claim 1, wherein the first and second phospholipids are phosphatidyl cholines.

24. A formulated liposome for incorporating a high content of hydrophobic substances therein, comprising:
  a first phospholipid which is optionally a phosphatidyl choline, which is selected from the group consisting of a hydrogenated naturally-occurring phospholipid and a saturated phospholipid having long carbon chains ($—(CH2)_n—$, in which n is at least 14), and which has a phase transition temperature $T_{g1}$ ranging between 40 and 74° C.;
  a second phospholipid which is optionally a phosphatidyl choline, which is selected from the group consisting of an unsaturated phospholipid and a saturated phospholipid having short carbon chains ($—(CH2)_n—$, in which n is at most 14, and which has a phase transition temperature $T_{g2}$ ranging between −30 and 10° C.;
  liposome-forming materials effective to form a liposome in which the first phospholipid and the second phospholipid coexist in two immiscible phases and create several discontinuous regions; and
  one or more hydrophobic substances incorporated in the liposome in an amount of at least 20 mole % to form the formulated liposome, wherein a drug delivery temperature $T_1$ and a drug storage temperature $T_2$ are chosen at specified ranges subject to an order of $T_{g1}>T_1>T_2>T_{g2}$, and wherein the formulated liposome has an incorporation efficiency which remains at least about 70% of incorporation efficiency for six months or more.

25. The formulated liposome according to claim 24, wherein the phase transition temperature of the first phospholipid ranges from 50 to 65° C., and the phase transition temperature of the second phospholipid ranges from −20 to 4° C.

26. The formulated liposome according to claim 24, wherein the first phospholipid is a phosphatidyl choline (PC) and is selected from the group consisting of hydrogenated egg phosphatidyl choline (HEPC), hydrogenated soy phosphatidyl choline (HSPC), dipalmitoyl phosphatidyl choline (DPPC) and distearyloyl phosphatidyl choline (DSPC).

27. The liposome according to claim 24, wherein the second phospholipid is a phosphatidyl choline (PC) and is selected from the group consisting of egg phosphatidyl choline (EPC), soy phosphatidyl choline (SPC), synthetic or natural-occurring unsaturated phosphatidyl cholines and dilauroyl phosphatidyl choline (DLPC), oleoyl palmitoyl phosphatidyl choline, dioleoyl phosphatidyl choline, and dipetroselinoyl phosphatidyl choline, dipalmitelaidoyl phosphatidyl choline.

28. The formulated liposome according to claim 24, wherein the hydrophobic substances are one or more hydrophobic pharmaceutical compounds.

29. The formulated liposome according to claim 28, wherein the one or more hydrophobic pharmaceutical compound is paclitaxel.

30. The formulated liposome according to claim 29, wherein the paclitaxel is incorporated with a drug/lipid ratio ranging from at least 20 mole % to 25 mole %.

31. The formulated liposome according to claim 30, wherein the paclitaxel is incorporated with a drug/lipid ratio ranging from at least 20 mole % to 25 mole % when the first phospholipid is hydrogenated egg phosphatidyl choline (HEPC) and the second phospholipid is egg phosphatidyl choline (EPC).

32. The formulated liposome according to claim 30, wherein the paclitaxel is incorporated with a drug/lipid ratio ranging from at least 20 mole % to 25 mole % when the first phospholipid is hydrogenated soy phosphatidyl choline (HSPC) and the second phospholipid is egg phosphatidyl choline (EPC).

33. The formulated liposome according to claim 28, wherein the one or more hydrophobic pharmaceutical compound is retinoic acid.

34. The formulated liposome according to claim 33, wherein the retinoic acid is incorporated with a drug/lipid ratio ranging from at least 20 mole % to 40 mole %.

35. The formulated liposome according to claim 34, wherein the retinoic acid is incorporated with a drug/lipid ratio ranging from at least 20 mole % to 40 mole % when the first phospholipid is hydrogenated soy phosphatidyl choline (HSPC) and the second phospholipid is egg phosphatidyl choline (EPC).

36. The formulated liposome according to claim 28, wherein the one or more hydrophobic pharmaceutical compound is camptothecin.

37. The formulated liposome according to claim 36, wherein the camptothecin is incorporated with a drug/lipid ratio ranging from at least 20 mole % to 30 mole %.

38. The formulated liposome according to claim 37, wherein the camptothecin is incorporated with a drug/lipid ratio ranging from at least 20 mole % to 30 mole % when the first phospholipid is hydrogenated egg phosphatidyl choline (HEPC) and the second phospholipid is egg phosphatidyl choline (EPC).

39. The formulated liposome according to claim 28, wherein the one or more hydrophobic pharmaceutical compound is selected from the group consisting of paclitaxel, retinoic acid, and camptothecin.

40. The formulated liposome according to claim 24, wherein the liposome-forming materials are selected from the group consisting of hydrophilic polymer-modified lipids, cholesterol, antioxidant, and mixture thereof.

41. The formulated liposome according to claim 40, wherein the hydrophilic polymer-modified lipid is methoxy polyethylene glycol-distearyloyl phosphatidyl ethanolamine (MPEG-DSPE).

42. The formulated liposome according to claim 24, wherein the one or more hydrophobic substances incorporated in the liposome is present in an amount ranging from at least 20 mole % to about 25 mole %.

43. The formulated liposome according to claim 24, wherein the one or more hydrophobic substances incorporated in the liposome is present in an amount ranging from at least 20 mole % to about 25 mole %.

44. The formulated liposome according to claim 24, wherein the first phospholipid and the second phospholipid are present in a molar ratio of the first phospholipid to the second phospholipid is at least 3:16.

* * * * *